US008556417B2

(12) United States Patent
Das et al.

(10) Patent No.: US 8,556,417 B2
(45) Date of Patent: Oct. 15, 2013

(54) APODIZED HYBRID DIFFRACTIVE-REFRACTIVE IOL FOR PSEUDO-ACCOMMODATION

(75) Inventors: Kamal K. Das, Arlington, TX (US); Mutlu Karakelle, Fort Worth, TX (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/364,911

(22) Filed: Feb. 2, 2012

(65) Prior Publication Data

US 2013/0201445 A1    Aug. 8, 2013

(51) Int. Cl.
*G02C 7/00*    (2006.01)
(52) U.S. Cl.
USPC ..................................................... 351/159.44
(58) Field of Classification Search
USPC ............ 351/159, 161, 168, 171, 159.44, 160; 359/570; 623/6.24
See application file for complete search history.

(56) References Cited

U.S. PATENT DOCUMENTS

| 2010/0066973 | A1  | 3/2010 | Portney |
| 2010/0097569 | A1* | 4/2010 | Weeber et al. ................ 351/169 |
| 2010/0131060 | A1* | 5/2010 | Simpson et al. ............. 623/6.24 |

* cited by examiner

*Primary Examiner* — Scott J Sugarman
*Assistant Examiner* — Mustak Choudhury
(74) *Attorney, Agent, or Firm* — Keiko Ichiye

(57) ABSTRACT

In certain embodiments, an ophthalmic lens comprises an optic. The optic has an optical axis and surfaces comprising an anterior surface and a posterior surface. At least one of the surfaces has an inner refractive region and a refractive-diffractive structure disposed outwardly from the inner refractive region in a direction away from the optical axis. The inner refractive region is adapted to contribute refractively to a distance focus optical power. The refractive-diffractive structure comprises one or more diffractive regions and one or more refractive regions. A diffractive region is adapted to contribute diffractively to a multi-zone optical power, and a refractive region is adapted to contribute refractively to the distance focus optical power.

19 Claims, 4 Drawing Sheets

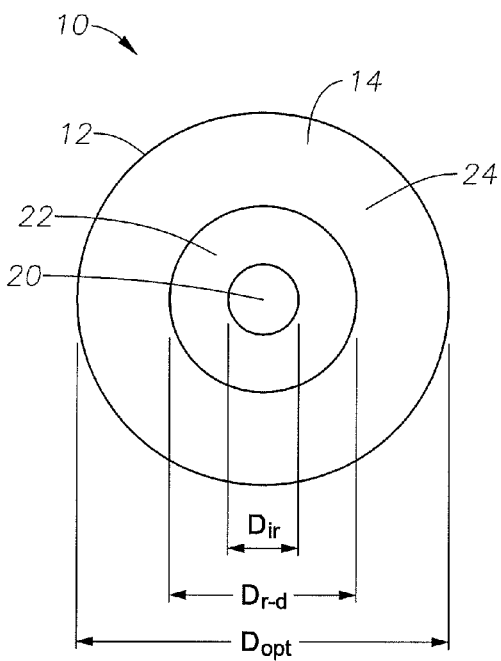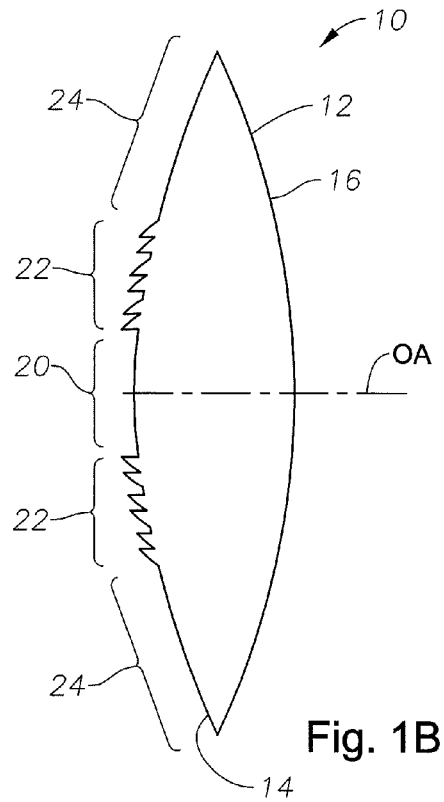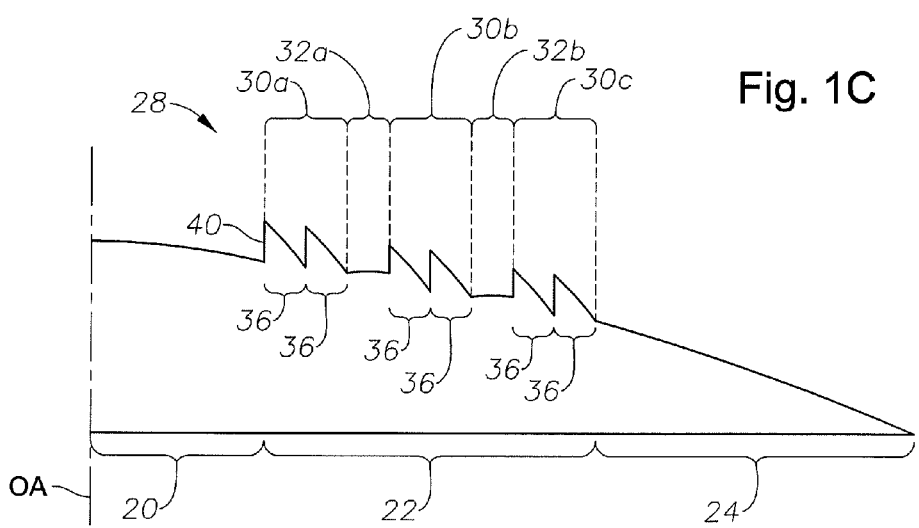

APODIZED HYBRID DIFFRACTIVE-REFRACTIVE IOL FOR PSEUDO-ACCOMMODATION

TECHNICAL FIELD

The present disclosure relates generally to ophthalmic lenses, and more particularly to an apodized hybrid diffractive-refractive intraocular lens (IOL) for pseudo-accommodation.

BACKGROUND

An IOL can be implanted into an eye during cataract surgery to replace the natural crystalline lens. Ciliary muscles vary the optical power of the natural crystalline lens to provide accommodation for viewing objects at different distances from the eye. Many IOLs, however, provide a monofocal power with no provision for accommodation. Certain multifocal IOLs provide a distance optical power as well as a near optical power (e.g., by employing diffractive structures) to yield a degree of pseudo-accommodation.

BRIEF SUMMARY

In certain embodiments, an ophthalmic lens comprises an optic. The optic has an optical axis and surfaces comprising an anterior surface and a posterior surface. At least one of the surfaces has an inner refractive region and a refractive-diffractive structure disposed outwardly from the inner refractive region in a direction away from the optical axis. The inner refractive region is adapted to contribute refractively to a distance focus optical power. The refractive-diffractive structure comprises one or more diffractive regions and one or more refractive regions. A diffractive region is adapted to contribute diffractively to a multi-zone optical power, and a refractive region is adapted to contribute refractively to the distance focus optical power.

BRIEF DESCRIPTION OF THE DRAWINGS

Exemplary embodiments of the present disclosure will now be described by way of example in greater detail with reference to the attached figures, in which:

FIGS. 1A through 1C schematically illustrate a hybrid diffractive-refractive intraocular lens (IOL) in accordance with certain embodiments:

FIG. 1A illustrates a view towards an anterior surface of the IOL, FIG. 1B illustrates a cross-section of the IOL, and FIG. 1C illustrates a more detailed view of the cross-section of the IOL;

DESCRIPTION OF EXAMPLE EMBODIMENTS

Figure 2:
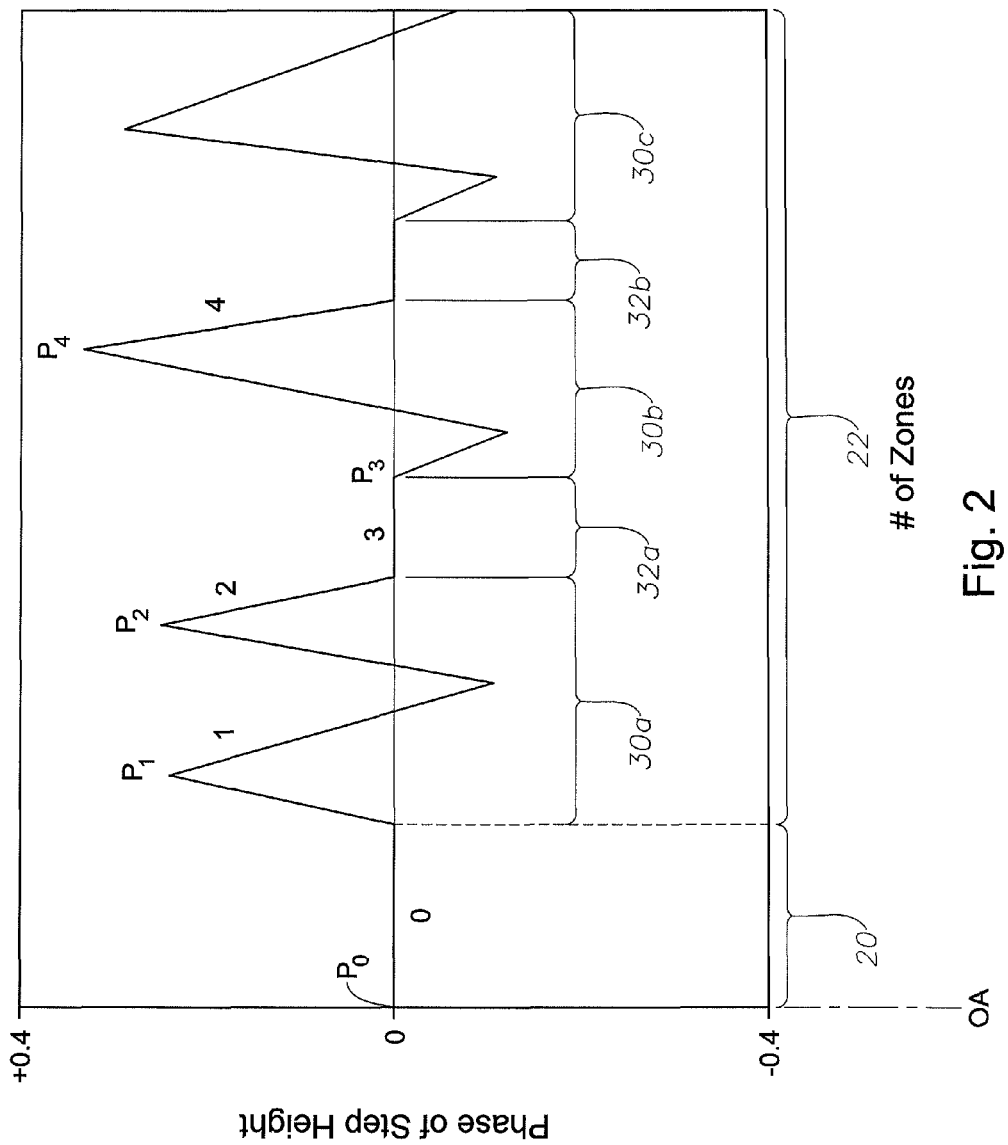
FIG. 2 illustrates an example of a profile of an inner refractive region and a refractive-diffractive structure.

Referring now to the description and drawings, example embodiments of the disclosed apparatuses, systems, and methods are shown in detail. The description and drawings are not intended to be exhaustive or otherwise limit or restrict the claims to the specific embodiments shown in the drawings and disclosed in the description. Although the drawings represent possible embodiments, the drawings are not necessarily to scale and certain features may be exaggerated, removed, or partially sectioned to better illustrate the embodiments.

FIGS. 1A through 1C schematically illustrate a hybrid diffractive-refractive intraocular lens (IOL) 10 in accordance with certain embodiments. FIG. 1A illustrates a view towards an anterior surface 14 of IOL 10, FIG. 1B illustrates a cross-section of IOL 10, and FIG. 1C illustrates a more detailed view of the cross-section of IOL 10.

Hybrid diffractive-refractive IOL 10 includes a mixture of diffractive and refractive regions that allow for multi-zone vision. "Multi-zone" refers to two or three of any of the following distances of vision: near, intermediate, and far (or distance) vision. Near vision refers to vision for near objects approximately 2 or fewer feet away from the eye. Intermediate vision refers to vision for intermediate objects approximately 2 to 20 feet (such as 2 to 3 feet) away from the eye. Distance vision refers to vision for distant objects approximately 20 or more feet away from the eye. "Nearer vision" may include near vision and intermediate vision.

A region of IOL 10 may contribute to the optical power of a zone to provide vision for that zone by focusing light rays from an object of the zone onto a focal point on the retina. For example, a region may contribute to a near focus optical power to provide near vision by focusing light rays from a near object onto a near focal point, may contribute to an intermediate focus optical power to provide intermediate vision by focusing light rays from an intermediate object onto an intermediate focal point, and/or may contribute to a distance focus optical power to provide distance vision by focusing light rays from a distant object onto a distance focal point.

IOL 10 includes an optic. Optic 12 can have any suitable diameter $D_{opt}$, e.g., in a range of 5 to 7 mm, such as 5.5 to 6.5 mm, e.g., approximately 6 mm. Optic 12 may comprise any suitable biocompatible material, such as a biocompatible polymeric material. Examples include, without limitation, a soft acrylic material (such as ACRYSOF, a cross-linked copolymer of 2-phenylethyl acrylate and 2-phenylethyl methacrylate), silicone, and hydrogel. The material may include optical filters that may improve visual acuity and/or protect retinal tissue from potentially harmful wavelengths. Though not shown, IOL 10 can also include one or more fixation members (e.g., haptics) that can facilitate placement of IOL 10 into a patient's eye.

Optic 12 has an anterior surface 14 and a posterior surface 16 substantially centered about an optical axis OA. Anterior surface 14 and posterior surface 16 may have any suitable base profile. In the illustrated example, each surface 14, 16 has a convex base profile. In other embodiments, one or both surfaces may have a concave or flat base profile. The nominal optical power of optic 12 can be determined from the base profiles in combination with the index of refraction of the material forming optic 12. In certain embodiments, the nominal optical power can be the monofocal refractive power of optic 12 for pupils with diameters less than the diameter $D_{ir}$ of inner refractive region 20 (described below).

In certain embodiments, anterior surface 14 has an auxiliary profile in addition to the base profile. In the example, the auxiliary profile of the anterior surface 14 includes an inner refractive region 20, a refractive-diffractive structure 22, and an outer refractive region 24. Inner refractive region 20 is disposed about optical axis OA, and diameter $D_{ir}$ of inner refractive region 20 may have any suitable value, such as a value in any of the following ranges: 0.8 to 1 mm, 0.90 to 1.0 mm, e.g., approximately 0.938 mm.

Inner refractive region 20 may be adapted to contribute refractively to a distance focus optical power. Inner refractive region 20 may refractively contribute to a distance focus optical power by bending light rays from a distant object to focus the rays onto a distance focal point on the retina to provide distance vision.

In certain embodiments, inner refractive region 20 may provide certain advantages. For example, in general, a refractive region allows more energy transmission than a diffractive region. Thus, an IOL with an inner refractive region 20 allows more energy transmission than an IOL with a central diffractive region. As another example, a refractive region has higher tolerance than a diffractive region to the location where light beams enter the region and to small refractive error. Thus, an IOL with an inner refractive region 20 has a higher tolerance to decentration of the IOL in the eye than an IOL with a central diffractive region.

Refractive-diffractive structure 22 is disposed outwardly from the inner refractive region 20 in a direction away from optical axis OA. The diameter $D_{r-d}$ of refractive-diffractive structure 22 may have any suitable value, such as 3 to 4 mm, 3.2 to 3.8 mm, or 3.3 to 3.5 mm, e.g., approximately 3.4 mm. In certain embodiments, diameter $D_{r-d}$ may not be larger than the diameter of an average pupil. For larger pupils, more energy may be directed to outer refractive region 24 for distance focus to minimize a halo effect.

In certain embodiments, refractive-diffractive structure 22 comprises one or more diffractive regions 30 (30a-c) and one or more refractive regions 32 (32a-b). A diffractive region 30 may be adapted to contribute diffractively by diffracting light rays with a diffraction grating to provide multi-zone vision. Diffractive region 30 may contribute to a multi-zone optical power as described above. A refractive region 32 may be adapted to contribute refractively to a distance focus optical power in a manner similar to that of inner refractive region 20.

In certain embodiments, a diffractive region 30 has a series of concentric rings that form a diffraction grating. The diffraction grating bends light rays to focus light at two places simultaneously to yield two separate focal points, such as any two of the following: distance, intermediate, and near focal points. Diffractive regions 30 have steps (or echelettes) 36 of particular step heights 40 that diffract light into one or more orders. The location of steps 36 determines the add power, and the step height 40 of each step 36 controls the proportion of light that is directed to the focal points. In general, higher steps 36 direct more light towards a near focal point and lower steps 36 direct more light towards a distance focal point.

Steps 36 may have any suitable step heights 40. In certain embodiments, steps 36 are apodized such that step heights 40 generally decrease with increasing distance from the optical axis OA. For example, step heights 40 may be 1.3 microns towards the center and decrease to 0.2 microns towards the perimeter. Steps 36 may be apodized in any suitable manner. In certain embodiments, steps 36 across different diffractive regions 30 may be strictly apodized such that step heights 40 decrease (or at least do not increase) with increasing distance from the optical axis OA. In other embodiments, steps 36 across different diffractive regions 30 may be generally apodized such that most step heights 40 decrease (or at least do not increase) with increasing distance from the optical axis OA, but at least one step height of a "non-apodized" step that is farther away from the optical axis OA is greater that a step height of a step that is closer to the optical axis OA. In yet other embodiments, steps 36 within a diffractive region 30 may be apodized, but steps 36 across different diffractive regions 30 need not be (but can be) apodized. For example, step heights 40 of diffractive region 30a may decrease as the distance from the optical axis OA increase, and step heights 40 of diffractive region 30b may similarly decrease, but the height of a non-apodized step 36 of diffractive region 30b may be greater than that of a step 36 of diffractive region 30a.

In certain embodiments, apodization yields a gradual transition of light between the distance, intermediate, and near focal points. In the embodiments, the higher steps 36 direct more light to the near focal point and the lower steps 36 direct more light to the distance focal point. A gradual energy blend between powers leads to smaller and smaller defocus points. In short, as light passes through a diffractive region 30, steps 36 yield waves that intersect at different focal points to form distinct images.

Light energy may be distributed in any suitable manner. For example, X% may be directed to the distance focal point, and Y% may be directed to the near focal point, where X is 50 or greater, such as 55 to 65, e.g., approximately 60, such as 58.9, and Y is 50 or less, such as 20 to 30, e.g., approximately 26, such as 25.5.

Step heights 40 may be calculated in any suitable manner. For example, the step height H may be calculated according to Equation (1):

$$H = \frac{P\lambda}{(n_{IOL} - n_{med})} \quad (1)$$

where P is the phase height, $\lambda$ is the design wavelength, $n_{IOL}$ is the refractive index of the IOL, and $n_{med}$ is the refractive index of the medium in which the IOL is placed. The design wavelength may be a narrow region of the visible spectrum that is used to determine optical performance of an IOL to minimize chromatic aberrations. P can be generalized as $P_m$, where m=0, 1, 2, 3, . . . . Parameter m may be selected according to the add power and/or outer apodized zone boundary. If wavelength $\lambda$, IOL refractive index $n_{IOL}$, and medium refractive index $n_{med}$ are constant, then $P_m$ can be used to represent the step height.

An outer refractive region 19 of the anterior surface extends from the outer boundary of refractive-diffractive structure 22 to the periphery of optic 12. Outer refractive region 19 may contribute refractively to a distance focus optical power for large pupil sizes, e.g., in low light conditions.

In certain embodiments, optic 12 may provide a higher modulation transfer function (MTF) value compared to known IOLs. Optic 12 may achieve a functional reading of 20/40 or better at near distance for an average pupil.

FIG. 2 illustrates an example of a profile of an inner refractive region 20 and a refractive-diffractive structure 22. In the example, refractive-diffractive structure 22 comprises diffractive regions 30 (30a-c) and refractive regions 32 (32a-b). Diffractive regions 30 have steps 1 through 4 with step heights $P_1$ through $P_4$. Step 4 is a non-apodized step. Step 4 farther away from optical axis OA than step 1, but step height $P_4$ is greater than step height $P_1$. In certain embodiments, step heights $P_0$ and $P_3$ may be the same.

Figure 3:
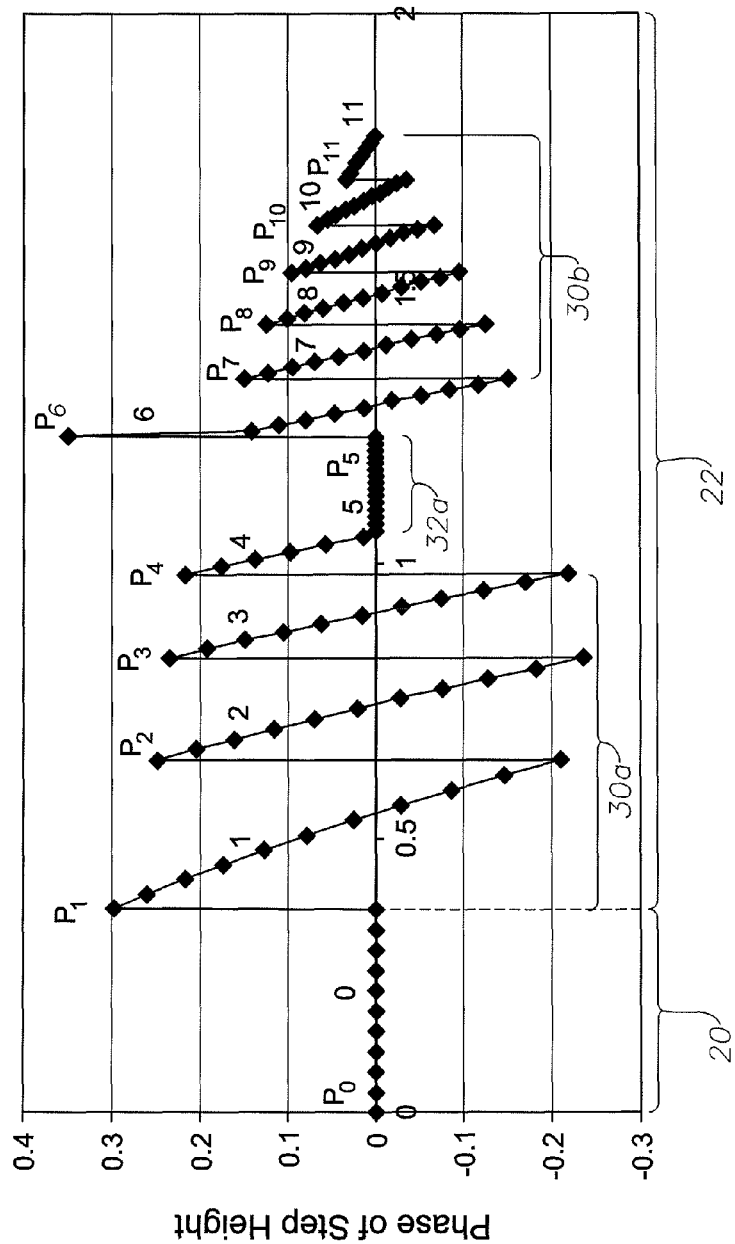
FIG. 3 illustrates another example of a profile of an inner refractive region and a refractive-diffractive structure.

FIG. 3 illustrates another example of a profile of an inner refractive region 20 and a refractive-diffractive structure 22. In the example, refractive-diffractive structure 22 comprises diffractive regions 30 (30a-b) and refractive region 32 (32a). Diffractive regions 30 have steps 1 through 11 with step heights $P_1$ through $P_{11}$. Step 6 is a non-apodized step. Step 6 farther away from optical axis OA than steps 1 through 4, but step height $P_6$ is greater than step heights $P_1$ through $P_4$.

Figure 4:
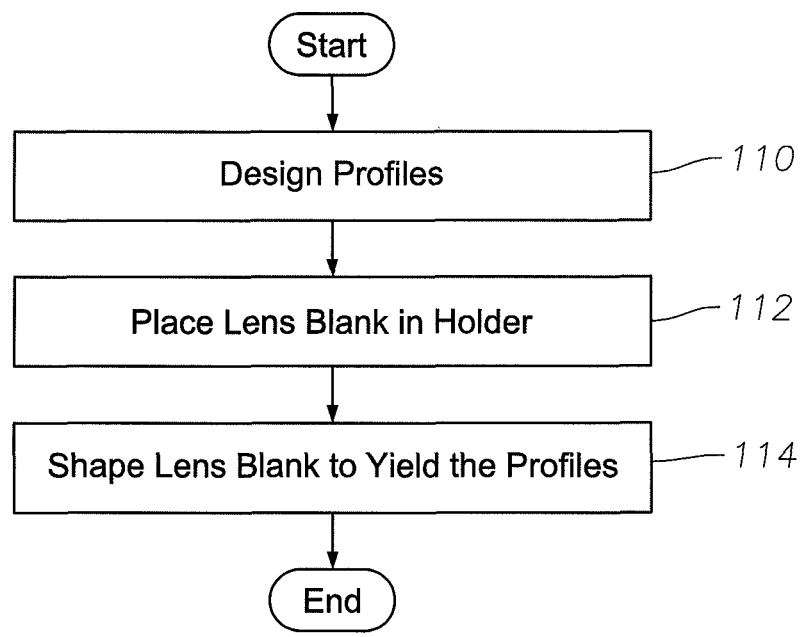
FIG. 4 illustrates an example of a method of making an optic of a hybrid diffractive-refractive IOL.

FIG. 4 illustrates an example of a method of making optic 12 of hybrid diffractive-refractive IOL 10. Optic 12 may be manufactured according to any suitable method. In certain embodiments, the profiles of the surfaces are designed at step 110, and then optic 12 with the profiles is manufactured using any suitable manner. In certain embodiments, a lens blank is placed in a lens holder at step 112. The lens blank is then shaped at step 114 to yield the profiles. Suitable shaping techniques may include any method of formation suitable to the materials, including but not limited to molding, ablating, and/or lathing.

In one example, a method comprises placing a lens blank is a lens holder. The lens blank is shaped to yield an optic having an optical axis and a plurality of surfaces comprising an anterior surface and a posterior surface. The shaping includes shaping at least one of the surfaces to yield an inner refractive region and a refractive-diffractive structure disposed outwardly from the inner refractive region in a direction away from the optical axis. The inner refractive region is adapted to contribute refractively to a distance focus optical power. The refractive-diffractive structure comprises one or more diffractive regions and one or more refractive regions. A diffractive region is adapted to contribute diffractively to a multi-zone optical power, and a refractive region is adapted to contribute refractively to the distance focus optical power.

The profile of an IOL 10 may be calculated by a component that may include an interface, logic, memory, and/or other suitable element, any of which may include hardware and/or software. An interface can receive input, send output, process the input and/or output, and/or perform other suitable operations. Logic can perform the operations of a component, for example, execute instructions to generate output from input. Logic may be encoded in memory and may perform operations when executed by a computer. Logic may be a processor, such as one or more computers, one or more microprocessors, one or more applications, and/or other logic. A memory can store information and may comprise one or more tangible, computer-readable, and/or computer-executable storage medium. Examples of memory include computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server), and/or other computer-readable media.

In particular embodiments, calculation of the profile of the IOL 10 may be performed by one or more computer readable media encoded with a computer program, software, computer executable instructions, and/or instructions capable of being executed by a computer. In particular embodiments, the operations may be performed by one or more computer readable media storing, embodied with, and/or encoded with a computer program and/or having a stored and/or an encoded computer program.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

Other modifications are possible without departing from the scope of the invention. For example, the description illustrates embodiments in particular practical applications, yet other applications will be apparent to those skilled in the art. In addition, future developments will occur in the arts discussed herein, and the disclosed systems, apparatuses, and methods will be utilized with such future developments.

The scope of the invention should not be determined with reference to the description. In accordance with patent statutes, the description explains and illustrates the principles and modes of operation of the invention using exemplary embodiments. The description enables others skilled in the art to utilize the systems, apparatuses, and methods in various embodiments and with various modifications, but should not be used to determine the scope of the invention.

The scope of the invention should be determined with reference to the claims and the full scope of equivalents to which the claims are entitled. All claims terms should be given their broadest reasonable constructions and their ordinary meanings as understood by those skilled in the art, unless an explicit indication to the contrary is made herein. For example, use of the singular articles such as "a," "the," etc. should be read to recite one or more of the indicated elements, unless a claim recites an explicit limitation to the contrary. As another example, "each" refers to each member of a set or each member of a subset of a set, where a set may include zero, one, or more than one element. In sum, the invention is capable of modification, and the scope of the invention should be determined, not with reference to the description, but with reference to the claims and their full scope of equivalents.

What is claimed is:

1. An ophthalmic lens, comprising:
   an optic having an optical axis and a plurality of surfaces comprising an anterior surface and a posterior surface, at least one of the surfaces having:
   an inner refractive region adapted to contribute refractively to a distance focus optical power;
   a refractive-diffractive structure disposed outwardly from the inner refractive region in a direction away from the optical axis, the refractive-diffractive structure comprising two or more diffractive regions and one or more refractive regions, a diffractive region comprising a plurality of concentric rings that form a diffraction grating, at least one refractive region disposed between two diffractive regions, a diffractive region adapted to contribute diffractively to a multi-zone optical power, a refractive region adapted to contribute refractively to the distance focus optical power; and
   an outer refractive region disposed outwardly from the refractive-diffractive structure in the direction away from the optical axis, the outer refractive region adapted to contribute refractively to the distance focus optical power.

2. The ophthalmic lens of claim 1, at least one diffractive region adapted to contribute diffractively to an intermediate focus optical power.

3. The ophthalmic lens of claim 1, at least one diffractive region adapted to contribute diffractively to a near focus optical power.

4. The ophthalmic lens of claim 1, the one or more diffractive regions comprising:
   a first diffractive region adapted to contribute diffractively to an intermediate focus optical power; and
   a second diffractive region adapted to contribute diffractively to a near focus optical power.

5. The ophthalmic lens of claim 1, the refractive-diffractive structure having a diameter of 3.3 to 3.5 millimeters.

6. The ophthalmic lens of claim 1, at least one diffractive region comprising a plurality of apodized steps.

7. The ophthalmic lens of claim 1, at least one diffractive region comprising a plurality of apodized steps, at least two steps having the same height.

8. The ophthalmic lens of claim 1, the one or more diffractive regions comprising a plurality of strictly apodized steps.

9. The ophthalmic lens of claim 1, the one or more diffractive regions comprising a plurality of generally apodized steps and a non-apodized step.

10. An ophthalmic lens, comprising:
an optic having an optical axis and a plurality of surfaces comprising an anterior surface and a posterior surface, at least one of the surfaces having:
an inner refractive region adapted to contribute refractively to a distance focus optical power;
a refractive-diffractive structure disposed outwardly from the inner refractive region in a direction away from the optical axis, the refractive-diffractive structure comprising one or more diffractive regions and one or more refractive regions, a diffractive region comprising a plurality of concentric rings that form a diffraction grating, at least one refractive region disposed between two diffractive regions, a diffractive region adapted to contribute diffractively to a multi-zone optical power, a refractive region adapted to contribute refractively to the distance focus optical power, the refractive-diffractive structure having a diameter of 3.3 to 3.5 millimeters; and
an outer refractive region disposed outwardly from the refractive-diffractive structure in the direction away from the optical axis, the outer refractive region adapted to contribute refractively to the distance focus optical power.

11. The ophthalmic lens of claim 10, at least one diffractive region adapted to contribute diffractively to an intermediate focus optical power.

12. The ophthalmic lens of claim 10, at least one diffractive region adapted to contribute diffractively to a near focus optical power.

13. The ophthalmic lens of claim 10, the one or more diffractive regions comprising:
a first diffractive region adapted to contribute diffractively to an intermediate focus optical power; and
a second diffractive region adapted to contribute diffractively to a near focus optical power.

14. The ophthalmic lens of claim 10, at least one diffractive region comprising a plurality of apodized steps, at least two steps having the same height.

15. The ophthalmic lens of claim 10, the one or more diffractive regions comprising a plurality of strictly apodized steps.

16. The ophthalmic lens of claim 10, the one or more diffractive regions comprising a plurality of generally apodized steps and a non-apodized step.

17. A method comprising:
placing a lens blank is a lens holder; and
shaping the lens blank to yield an optic having an optical axis and a plurality of surfaces comprising an anterior surface and a posterior surface,
the shaping comprising shaping at least one of the surfaces to yield:
an inner refractive region adapted to contribute refractively to a distance focus optical power; and
a refractive-diffractive structure disposed outwardly from the inner refractive region in a direction away from the optical axis, the refractive-diffractive structure comprising one or more diffractive regions and one or more refractive regions, a diffractive region comprising a plurality of concentric rings that form a diffraction grating, at least one refractive region disposed between two diffractive regions, a diffractive region adapted to contribute diffractively to a multi-zone optical power, a refractive region adapted to contribute refractively to the distance focus optical power; and
an outer refractive region disposed outwardly from the refractive-diffractive structure in the direction away from the optical axis, the outer refractive region adapted to contribute refractively to the distance focus optical power.

18. The method of claim 17, the shaping comprising shaping the at least one of the surfaces to yield:
an outer refractive region disposed outwardly from the refractive-diffractive structure in the direction away from the optical axis, the outer refractive region adapted to contribute refractively to the distance focus optical power.

19. The method of claim 17, the shaping comprising shaping the at least one of the surfaces to yield the one or more diffractive regions comprising:
a first diffractive region adapted to contribute diffractively to an intermediate focus optical power; and
a second diffractive region adapted to contribute diffractively to a near focus optical power.

* * * * *